United States Patent [19]

Miller

[11] Patent Number: 5,300,033

[45] Date of Patent: Apr. 5, 1994

[54] INTRODUCER ASSEMBLY AND VALVE CONSTRUCTION FOR USE THEREIN

[75] Inventor: Gary H. Miller, Milpitas, Calif.

[73] Assignee: Unisurge, Inc., Cupertino, Calif.

[21] Appl. No.: 911,158

[22] Filed: Jul. 9, 1992

[51] Int. Cl.$^5$ ............................................. A61M 5/178
[52] U.S. Cl. ...................................... 604/167; 604/256; 251/149.1; 137/844
[58] Field of Search ............... 604/167, 164, 256, 905; 137/844, 843, 845, 846, 847; 251/149.1

[56] References Cited

U.S. PATENT DOCUMENTS

| | | | |
|---|---|---|---|
| 3,861,416 | 1/1975 | Wichterle | 137/525.3 |
| 3,964,509 | 6/1976 | Daubenberger | 137/844 |
| 4,177,814 | 12/1979 | Knepshield et al. | 128/348 |
| 4,222,126 | 9/1980 | Boretos et al. | 3/1.5 |
| 4,364,127 | 12/1982 | Pierce et al. | 3/1.5 |
| 4,673,393 | 6/1987 | Suzuki et al. | 604/167 |
| 4,715,360 | 12/1987 | Akui et al. | 604/256 |
| 4,857,062 | 8/1989 | Russell | 604/167 |
| 4,932,633 | 6/1990 | Johnson et al. | 604/256 |
| 4,946,133 | 8/1990 | Johnson et al. | 251/149.1 |
| 5,092,857 | 3/1992 | Fleischhacker | 604/167 |
| 5,102,395 | 4/1992 | Cheer et al. | 251/149.1 |
| 5,104,379 | 4/1992 | Nakamura et al. | 604/256 |
| 5,141,498 | 8/1992 | Christian | 604/167 |
| 5,176,648 | 1/1993 | Holmes et al. | 604/164 |

Primary Examiner—John G. Weiss
Attorney, Agent, or Firm—Flehr, Hohbach, Test, Albritton & Herbert

[57] ABSTRACT

Valve construction for use with an introducer assembly having a tubular member with a valve housing at one end thereof for receiving the valve construction to permit a medical instrument to be introduced therethrough. The valve construction is comprised of a body formed of an elastic material. The body has a cylindrical wall with an axially-extending bore. The body is provided with a first planar wall formed integral with the cylindrical wall and extending across the first end of the bore. The first wall has a centrally-disposed opening therein aligned with the bore. The body is also provided with a second wall formed integral with the cylindrical wall and extending across the second end of the bore. The second wall has a slit therein extending diametrically of the bore to provide first and second leaflets. The bore, the hole in the first planar wall and the slit in the second wall permitting a medical instrument to be introduced therethrough and through the tubular member with at least one seal being formed between the valve construction and the medical instrument. The second wall has inner and outer surfaces which are inclined outwardly from a plane extending perpendicular to the axis of the bore to avoid prolapse of the leaflets during removal of the instrument from the valve construction.

23 Claims, 2 Drawing Sheets

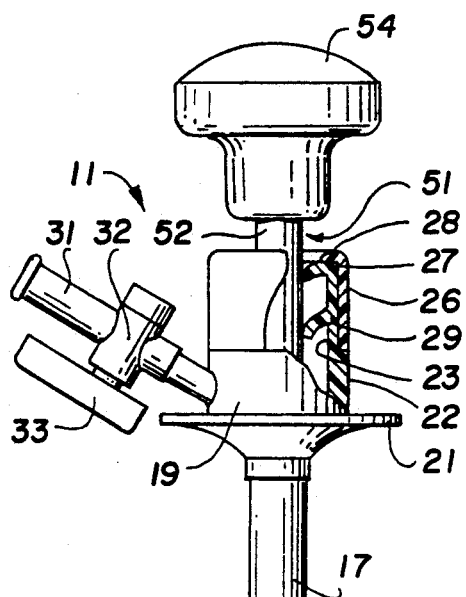
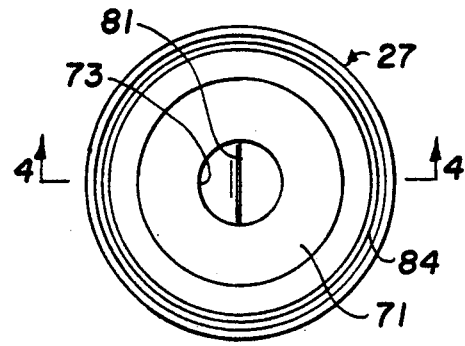
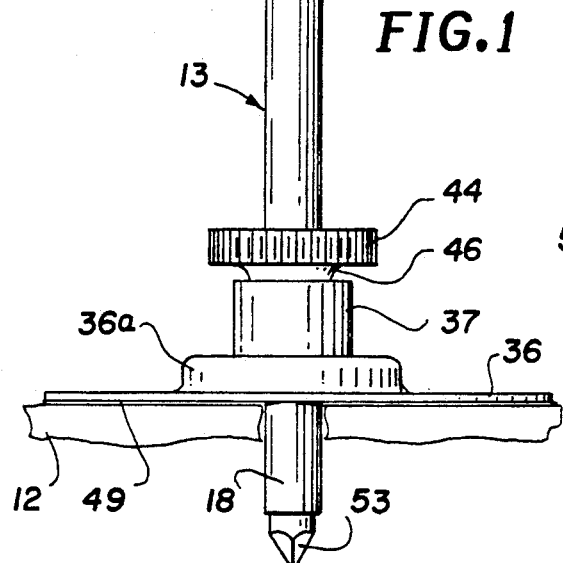
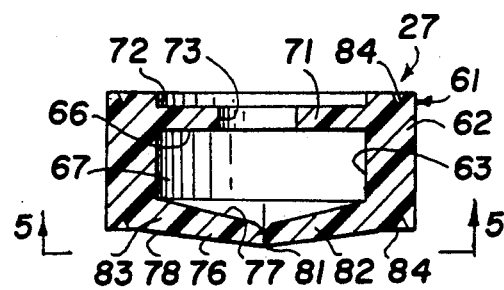
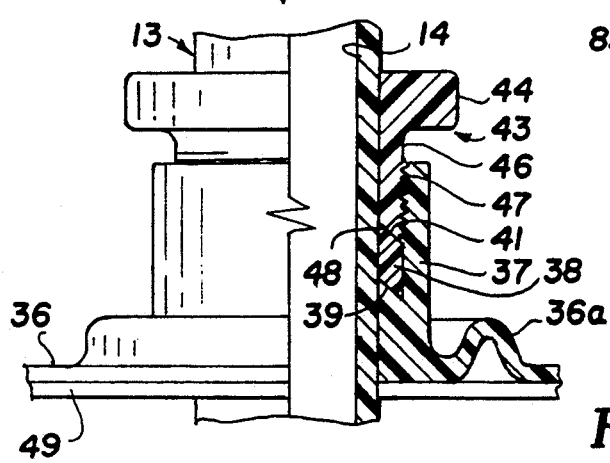
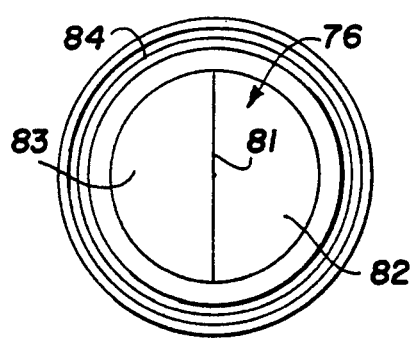
FIG.1
FIG.3
FIG.4
FIG.2
FIG.5

INTRODUCER ASSEMBLY AND VALVE CONSTRUCTION FOR USE THEREIN

This invention relates to an introducer assembly and valve construction for use therein.

An introducer assembly is disclosed in co-pending applications, Ser. No. 07/807,101, filed Dec. 13, 1991, and a valve in Ser. No. 07/757,343 filed Sep. 10, 1991 for use in the introducer assembly. In using such a valve in the introducer assembly it has been found in certain instances that an electrocautery hook catches onto one or more of the leaflets of the valve as the hook is being withdrawn causing the valve to prolapse and not maintain a good seal. There is, therefore, a need for a new and improved introducer assembly and a valve construction for use therein which will overcome this difficulty.

In general, it is an object of the present invention to provide an introducer assembly and a valve construction for use therein which can be utilized in various laparoscopic procedures in which hooks are utilized.

Another object of the present invention is to provide an introducer assembly for which good seals are maintained during introduction and withdrawal of laparoscopic instruments.

Another object of the present invention is to provide an introducer assembly and valve construction for use therein in which the valve construction resists prolapse.

Additional objects of the present invention will appear from the defined description in which preferred embodiments are set forth in detail in conjunction with the accompanying drawings.

In the Figures:

FIG. 1 is an elevational view partially in cross-section showing the introducer assembly with a valve construction for use therein incorporating the present invention.

FIG. 2 is an enlarged detail view partially in cross-section of a portion of the introducer assembly shown in FIG. 1.

FIG. 3 is a top plan view of the valve construction utilized in the introducer assembly shown in FIG. 1.

FIG. 4 is a cross-sectional view taken along the line 4—4 of FIG. 3.

FIG. 5 is a bottom plan view of the valve construction looking along the line 5—5 in FIG. 4.

Figure 8:
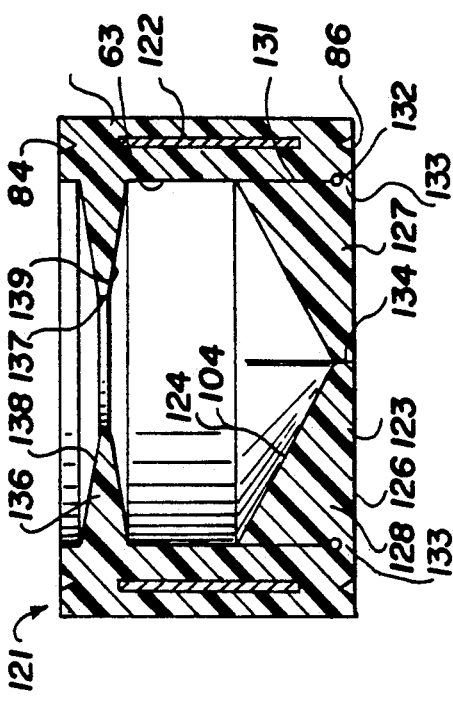
FIG. 8 is a cross-sectional view similar to FIGS. 6 and 7 showing another embodiment of a valve construction incorporating the present invention.

In general, the valve construction of the present invention is for use with an introducer assembly having a tubular member and with a housing at one end thereof for receiving the valve construction. The valve construction is comprised of a body formed of an elastic material and having an axially-extending bore with first and second ends. The body is provided with a cylindrical wall extending coaxially of the bore and defining the bore. The body is also provided with a first planar wall formed integral with the cylindrical wall and extending across the first end of the bore. The first planar wall has a centrally disposed opening in alignment with the bore. A second wall is provided which is formed integral with the cylindrical wall and extends across the second end of the bore and has a slit therein extending diametrically of the bore to provide first and second leaflets. The bore, the hole in the first planar wall and the slit in the second wall permit a medical instrument to be inserted therethrough and to be withdrawn therefrom while maintaining a good seal between the introducer assembly and the medical instrument. The second wall has inner and outer surfaces which are inclined outwardly from the plane extending perpendicular to the axis of the bore to inhibit prolapse of leaflets during removal of a medical instrument from the introducer assembly.

More in particular, the introducer assembly 11, as shown in FIG. 1, is very similar to the introducer assembly as shown in co-pending application, Ser. No. 07/807,101, filed Dec. 13, 1991. The introducer assembly is to be utilized for penetrating an abdominal wall 12 as shown in FIG. 1.

The introducer assembly 11 consists of a tubular member or cannula 13 and which is provided with an axially-extending bore 14. The sleeve or cannula 13 is provided with proximal and distal extremities 17 and 18. A housing 19 is mounted on the proximal extremity 17 and is secured thereto by suitable means such as an adhesive. The housing 19 is provided with an upwardly flared circular flange 21. The housing 19 is provided with a cylindrical wall 22 which has a cylindrical bore 23 therein that is in communication with the bore 14 of the cannula 13. A cylindrical cap 26 is then fitted onto the housing 19 in a suitable manner such as by friction-fit.

A valve construction 27 incorporating the present invention is disposed within the cap 26 with the outer extremity of the valve construction 27 being engaged by an annular lip 28 forming a part of the cap and with the lower extremity of the valve construction being engaged by a shoulder 29 provided by the upper extremity of the cylindrical wall 22. A Luer-type inlet fitting 31 is mounted at approximately a 45° angle in the housing 19 and is provided with a stopcock 32 which is provided with a handle 33 to permit opening and closing of the fitting 31.

A diaphragm 36 is adjustably positioned on the distal extremity 18 of the cannula 13 and is of the type described in co-pending application, Ser. No. 807,101, filed Dec. 13, 1991. The diaphragm 36 is provided with an annular convolution 36a which adjoins a centrally disposed hub 37 that has a lock ring 38 disposed therein (see FIG. 2). The lock ring 38 is provided with upwardly and inwardly inclined lower and upper surfaces 39 and 41 which are substantially parallel to each other. Surfaces 39 and 41 can be inclined at a suitable angle as, for example, 45°.

The cannula 13, the housing 19 and the cap 26 can be formed of a suitable plastic as, for example, Ultem 1,000. Diaphragm 36 can be formed with a suitable material such as Kraton. The lock ring 38 also can be formed of a suitable material such as Santoprene of about 45 durometer, Shore A.

A lock cap 43 formed of a suitable material such as Ultem 1,000 is provided with a knurled knob 44 and an externally-threaded cylindrical extension 46 which threadly engages internal threads 47 provided in the hub 37. The extension 46 is provided with a tapered surface 48 and which is adapted to seat against the surface 41 of the lock ring 38. Thus, it can be seen that by rotating the knob 44, the lock ring 38 can be compressed to form a liquid-tight and air-tight seal between a cannula 13 extending therethrough and the hub 37.

A layer 49 is provided on the lower surface of the diaphragm 36 and is formed of a suitable material such as a double-sided sticky adhesive formed to provide good adherence between the diaphragm 36 and the abdominal wall 12.

An obturator 51 is provided as part of the introducer assembly 11 and is provided with a shaft 52 of a suitable material such as stainless steel to provide a spike or a shaft which has a pointed distal extremity 53 thereon. A knob 54 of a suitable material such as plastic is mounted on the proximal extremity of the shaft 52. As can be seen, the obturator 51 is adapted to extend through the valve construction 27 and through the cannula 13 as shown in FIG. 1 with the valve construction 27 providing sealing means between the obturator 51 and the cannula 13 to prevent the escape of fluid between the cannula 13 and the obturator 51.

The valve construction 27 is shown in detail in FIGS. 3, 4, and 5 and, as shown therein, consists of a body 61. The body 61 is formed of a suitable elastomeric material such as silicone having a medium durometer as, for example, ranging from 40 to 70 shore A hardness. Preferably, it is desirable to utilize a hardness of 40 to 50 durometer shore A with a 100–200 pound per square inch, in tear strength. Other suitable materials can be utilized as, for example, heat-cured rubber. The silicone or rubber can be formed in a liquid injection molding process to form the body 61. The body 61 is provided with a cylindrical wall 62 which has a bore 63 extending axially therethrough. The bore 63 is provided with a first or upper end 66 and a second or lower end 67. The body 61 is formed with a first or upper wall 71 which is formed integral with the cylindrical wall 62 and extends across the upper or first end of the bore 66. As shown (see FIG. 4), the first wall 71 is substantially planar and is slightly recessed with respect to the uppermost extremity of the cylindrical wall 62 to form a cylindrical recess 72. A centrally disposed hole 73 is provided within the wall 71 and is in axial alignment with the axis of the bore 63. The hole 73 is sized so as to form a seal with respect to the obturator 51 when it is introduced therethrough.

The body 61 is also provided with a second or lower wall 76 which extends across the second or lower end 67 of the bore 63. The second or lower wall 76 is provided with inner and outer walls and with upper or inner and lower or outer surfaces 77 and 78 which are inclined outwardly from an imaginary plane extending perpendicular to the axis of the bore 63 at a suitable angle ranging from 0° to 85°. By way of example, as shown in FIG. 4, the surface 77 can then extend at an angle of 15° whereas the surface 76 can extend at an angle of 10°. By way of example, a valve construction of one type incorporating the present invention had a outside diameter of 0.750 inches and a bore 63 of 0.550 inches.

The second or lower wall 76 is provided with a diametrically-extending slit 81 so that two leaflets 82 and 83 are formed by the second or lower wall 76. The second or lower wall 76 is inclined upwardly and outwardly towards an apex to inhibit or minimize prolapse of the leaflets 82 and 83 during removal of an obturator 51 therefrom. This prolapse is inhibited by a keystone effect provided by the outwardly inclined leaflets 82 and 83 that provides a maximum sealing force at the slit 81. Thus, as can be seen from FIG. 1, first and second seals are provided when the obturator 51 is introduced through the valve construction into the cannula 13. The first seal is formed by leaflets 82 and 83 engaging the shaft 52. The other or second seal is formed by the wall 71 engaging the circumference of the shaft 52. As the obturator 51 is removed, the shape of the leaflets 82 and 83 permits the obturator 51 to be removed without causing prolapse of the leaflets 82 and 83 and thereby continuously maintaining a seal between the cannula 13 and the obturator 51. As soon as the obturator 51 is removed from the slit 81, the leaflets 82 and 83 will close to the position shown in FIG. 5 to form a fluid-tight seal. Thus, a good seal is provided even though the obturator is completely removed from the hole 73.

Additional sealing means is provided between the upper and lower extremities of the valve construction 27 and consists of annular recesses 84 and 86 provided in the cylindrical wall 62 on the upper and lower extremities of the same which are V-shaped in cross-section as shown in FIG. 4 to facilitate forming a good seal between the lip 28 and the shoulder 29.

Figure 6:
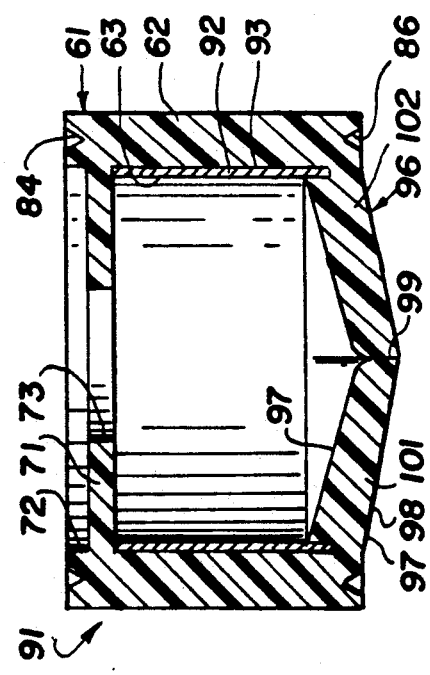
FIG. 6 is a cross-sectional view similar to FIG. 4 showing an alternative construction for the valve construction shown in FIGS. 3, 4 and 5.
Figure 7:
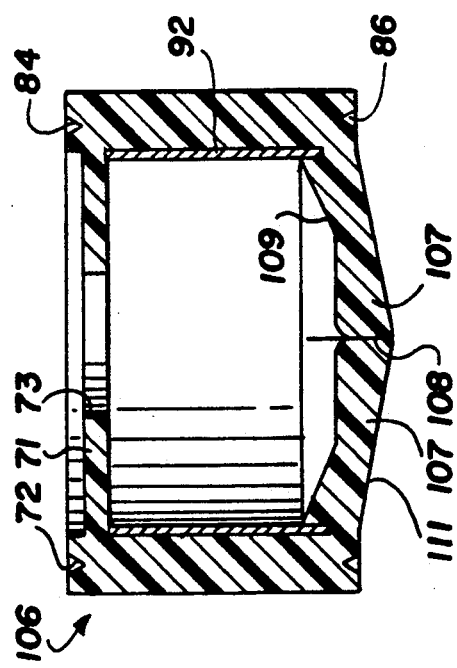
FIG. 7 is a cross-sectional view similar to FIG. 6 and showing another embodiment of the valve construction incorporating the present invention.

It has been found that when large medical instruments or tools are utilized in conjunction with the introducer assembly 11, there is a tendency for the large tools to cause the valve construction 27 to become non-circular and, thereby, tending to inhibit appropriate sealing action. As shown in FIG. 6, valve construction 91 very similar to the valve construction 11 hereinbefore described is provided to overcome this difficulty with the exception that a reinforcing ring 92 formed of a suitable material such as stainless steel has been molded in the body 61 and, as shown, is provided on inner surface 93 of the cylindrical wall 62 and extends the length of the bore 63. The ring 92 has its upper extremity terminating at the wall 71 and has its lower extremity extending into the second or lower wall as shown in FIG. 7. The ring 92 has a sufficient wall thickness to provide the desired rigidity as, for example, a thickness ranging from 0.015 to 0.020 inches. If a softer material such as brass is utilized, the ring can be thicker as, for example, 0.030 to 0.040 inches. If desired, the ring 92 can also be formed of a rigid plastic material.

By providing the reinforcing ring 92, the placement of a large trocar or obturator 51 through the valve construction 27 prevents the upper extremity of the body 61 from being pulled inwardly as the shaft 52 passes through the hole 73. This helps to ensure that a good seal is continuously maintained as the shaft 52 is passed through the valve construction 27.

The lower wall 96 has first or inner and second or lower surfaces 97 and 98 and a diametrically extending slit 99 to form leaflets 101 and 102. The leaflets 101 and 102 are thicker in cross section to provide an additional closing force at the slit 99.

Another embodiment of a valve construction 106 is shown in FIG. 7 in which a second or lower wall 107 is provided which is thicker in cross-section adjacent the diametrically extending slit 108. In addition, the upper and lower surfaces 109 and 111 of the thicker wall 107 are positioned such so that the surface 109 is then inclined at a greater angle as, for example, at an angle of 25° rather than the 15° for the surface 77. It has been found that this greater angle inhibits the obturator 51 from slicing or cutting the wall 109 forming the slit 108 to also help ensure that a good seal is maintained when the obturator or trocar 51 is being removed and after removal.

Still another embodiment of a valve construction 121 is shown in FIG. 8 in which a reinforcing ring 122 is embedded within the cylindrical wall 62. The valve construction 121 is provided with a thicker lower wall 123 which includes inner and outer walls and is provided with inner and or upper and outer or lower surfaces 124 and 126 respectively in which the surface 124 is inclined at a greater angle from the horizontal as, for example, 30° with the outer surface 126 being inclined at an angle of 0°. In order to permit easier bending of the leaflets 127 and 128, an annular or cylindrical cut or slice 131 is provided in the body 61 adjacent the wall 123 which terminates at its distal extremity in an annular bead 132 which is circular in cross-section as shown in FIG. 8. This bead 132 with the annular slice 131 provide a thinner wall portion to form hinges 133 for the leaflets 127 and 128 to facilitate less restrictive opening of the flaps or leaflets 127 and 128. Thus, easier opening of the leaflets 127 and 128 with a greater incline provided on the surface 124 helps to ensure that the trocar will not dissect or slit the lower wall 123 to thereby maintain the integrity of the sealed slit 134. The hinging of the leaflets 127 and 128 also serves to facilitate closing of the seal 124 when the obturator or trocar 51 is removed. The hinges 133 of the leaflets 127 and 128 facilitate the return of the leaflets 127 and 128 to their at-home position to provide a good seal.

As shown in FIG. 8, the valve construction 121 is provided with an upper wall 136 and a central opening 137. The upper wall 136 is tapered so that it becomes progressively thinner in cross-section in a direction towards the central opening 137 and terminating in a full radius at the opening 137 as shown. Thus, the upper and lower surfaces 138 and 139 can be inclined at an angle from the horizontal in opposite directions by a suitable angle such as 6°. The upper wall 136 has a rounded inner margin which circumscribes the central opening 137.

Figure 9:
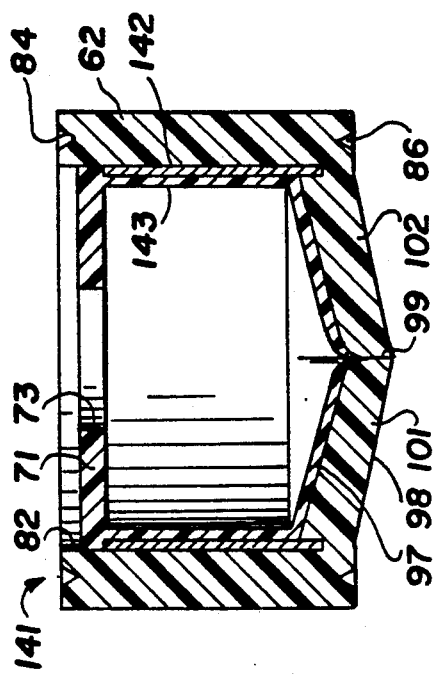
FIG. 9 is a cross-sectional view similar to FIGS. 6, 7 and 8 showing another embodiment of the valve construction incorporating the present invention.

Still another alternative valve construction 141 is shown in FIG. 9 in which a reinforcing ring 142 is provided as an insert adjacent the surface of the wall 62. A liner 143 formed of a elastomeric material similar to the elastomeric material utilized for the body 61 is provided but of a higher durometer, as for example, 60 to 80 durometer Shore A. It can be seen the liner 143 covers the ring 142 and also covers the surface 97. The liner of higher durometer material is provided to inhibit cutting of the valve construction by the obturator or trocar 51 when it is inserted through the valve construction 141. The liner 143 can have a suitable wall thickness as, for example, ranging from 0.03 to 0.030 inches. A higher durometer silicone or heat-cured rubber also can be utilized for this purpose. The liner 143 serves to inhibit the trocar or obturator 51 from cutting the valve flaps 101 and 102. The thickness of the liner 143 is thin enough so that it does not substantially affect the opening and closing of the leaflets 101 and 102 with respect to the slit 99.

From the foregoing, it can be seen that there has been provided a valve construction which can be utilized with an introducer assembly which serves to permit air or $C_2O$ or other gas introduced into the abdominal cavity during a laparoscopic procedure from escaping out past the trocar or other instrument introduced through the cannula 13. When a medical device or tool is in place in the introducer assembly, the hermetic seal is established by the upper wall 71 with the circular orifice or hole 73 therein. When the medical device has been removed from the cannula 13, the principal seal is established by the lower wall 76 which has the leaflets forming the seal along the slit. The valve construction is constructed in such a manner so that it cannot be accidentally cut or sliced by a trocar. Similarly, the valve construction is also constructed so that the leaflets cannot be grasped by hooks and the like. The small angle on the outside surface, as for example, 10° greatly reduces the possibility of grasping of the leaflets by a hook. The greater angle of the inside surface of the lower wall as, for example, 15° and greater is to ensure that the lower wall will not be inadvertently cut by the trocar. Also, this possible cutting by the trocar can be minimized or eliminated by utilizing a high durometer liner. By providing reinforcing members within the valve, the valve construction retains its shape during introduction and removal of the medical tools to thereby ensure that positive seals are maintained at all times during insertion and withdrawal of the medical tools or instruments. By providing an improved hinging action for the leaflets of the valve, it is possible to readily withdraw and remove the medical tool. It also helps to ensure that prolapse does not occur during withdrawal of the medical instrument.

I claim:

1. A valve construction for use with an introducer assembly having a tubular member with a valve housing at one end thereof for receiving the valve construction to permit a medical instrument to be introduced therethrough, the valve construction comprising a body formed of an elastic material, said body having a cylindrical wall with an axially-extending bore which has first and second ends, a first wall formed integral with the cylindrical wall and extending across the first end of the axially-extending bore, said first wall having a centrally-disposed opening therein aligned with said axially-extending bore, a second wall formed integral with the cylindrical wall and extending across the second end of the axially-extending bore, said second wall having a single slit therein extending therethrough diametrically of said axially-extending bore to provide first and second semicircular leaflets, said axially-extending bore, said opening in said first wall and said slit in the second wall when seated in said housing permitting a medical instrument to be introduced therethrough and through the tubular member with at least one seal being formed between the valve construction and the medical instrument, said second wall having inner and outer surfaces with at least the inner surface being inclined outwardly from a plane extending perpendicular to the axis of the axially-extending bore in a direction towards the axially-extending bore, each of said leaflets having an acruate base portion and a straight distal portion, said distal portion having a thickness which is less than the thickness of said base portion so as to permit the leaflets to flex and allow the instrument to pass therethrough, said distal portions of said leaflets having a substantial thickness and butting each other to provide a keystone-like seal so as to avoid prolapse of the leaflets during removal of the instrument from the valve construction and also to provide a more positive seal as pressure is applied to the outer surface of the second wall.

2. A valve construction as in claim 1 wherein said first wall has a cross section which decreases in thickness in a direction towards the centrally disposed opening.

3. A valve construction as in claim 2 wherein said first wall has an inner margin which circumscribes the centrally disposed opening and is rounded.

4. A valve construction of claim 1, wherein said outer surface is inclined from the plane extending perpendicular to the axis of the axially-extending bore in a direction towards the axially-extending bore at an angle of at least 0°.

5. A valve construction as in claim 4, wherein said outer surface is inclined at an angle ranging from 0° to 85° from the plane extending perpendicular to the axis of the axially-extending bore.

6. A valve construction as in claim 5, wherein said inner surface is inclined at an angle of at least 10° from the plane extending perpendicular to the axis of the axially-extending bore.

7. A valve construction as in claim 1, together with a cylindrical reinforcing member for reinforcing the same.

8. A valve construction as in claim 7, wherein said cylindrical wall has an inner surface and wherein said reinforcing member is disposed adjacent the inner surface of the cylindrical wall.

9. A valve construction as in claim 7, wherein said reinforcing member is disposed with the cylindrical wall.

10. A valve construction as in claim 1, wherein said inner surface is inclined outwardly from said plane at an angle which is greater than the angle at which said outer surface is inclined outwardly from said plane.

11. A valve construction for use with an introducer assembly having a tubular member with a valve housing at one end thereof for receiving the valve construction to permit a medical instrument to be introduced therethrough, the valve construction comprising a body formed of an elastic material, said body having a cylindrical wall with an axially-extending bore which has first and second ends, a first wall formed integral with the cylindrical wall and extending across the first end of the axially-extending bore, said first wall having a centrally-disposed opening therein aligned with said axially-extending bore, a second wall formed integral with the cylindrical wall and extending across the second end of the axially-extending bore, said second wall having a slit therein extending diametrically of said axially-extending bore and through the second wall to provide first and second semicircular leaflets, said axially-extending bore, said opening in the first wall and said slit in the second wall when seated in said housing permitting a medical instrument to be introduced therethrough and through the tubular member with at least one seal being formed between the valve construction and the medical instrument, said second wall having inner and outer surfaces with at least the inner surface being inclined outwardly from a plane extending perpendicular to the axis of the axially-extending bore in a direction towards the axially-extending bore to avoid prolapse of the leaflets during removal of the instrument from the valve construction and said second wall having a cylindrical slice therein which has an axis coincident with the axis of the axially-extending bore and extends outwardly from the inner surface to form a hinged region of reduced thickness for each of the leaflets.

12. A valve construction as in claim 11, wherein said cylindrical slice has a distal extremity and wherein said second wall is formed with a circular annular recess disposed at the distal extremity of the cylindrical slice.

13. A valve construction for use with an introducer assembly having a tubular member with a valve housing at one end thereof for receiving the valve construction to permit a medical instrument to be introduced therethrough, the valve construction comprising a body formed of an elastic material having a predetermined durometer, said body having a cylindrical wall with an axially-extending bore which has first and second ends, a first wall formed integral with the cylindrical wall and extending across the first end of the axially-extending bore, said first wall having a centrally-disposed opening therein aligned with said axially-extending bore, a second wall formed integral with the cylindrical wall and extending across the second end of the axially-extending bore, said second wall having a slit therein extending diametrically of said axially-extending bore and through the second wall to provide first and second semicircular leaflets, said axially-extending bore, said opening in the first wall and said slit in the second wall when seated in said housing permitting a medical instrument to be introduced therethrough and through the tubular member with at least one seal being formed between the valve construction and the medical instrument, said second wall having inner and outer surfaces with at least the inner surface being inclined outwardly from a plane extending perpendicular to the axis of the axially-extending bore in a direction towards the axially-extending bore to avoid prolapse of the leaflets during removal of the instrument from the valve construction, a liner disposed within said bore and covering said inner surface, said liner having a hardness greater than that of the material forming the body.

14. An introducer assembly for introducing medical instruments into the body, comprising a tubular member having proximal and distal extremities and a central bore therein, a housing mounted on the proximal extremity of the tubular member, said housing having a recess therein in alignment with said central bore in said tubular member, a valve construction disposed in said housing and having first and second seals, a cap mounted on said housing and serving to retain said valve construction in said housing, said valve construction having a body with integrally formed first and second spaced-apart walls, said first wall having an orifice therein and said second wall having a diametrically-extending slit therein to form first and second semicircular leaflets, said first and second walls permitting a medical instrument to be inserted therethrough and withdrawn therefrom while maintaining a seal between the instrument and the tubular member, said second wall having an inner surface which is inclined outwardly in a direction towards the axis of said central bore with respect to an imaginary plane extending perpendicular to the axis of the central bore, each of said leaflets having an arcuate base portion and a straight distal portion, said distal portion having a thickness which is less than the thickness of said base portion so as to permit the leaflets to flex and allow the instrument to pass therethrough, said distal portions of said leaflets having a substantial thickness and abutting each other to provide a keystone-like seal so as to avoid prolapse of the leaflets during removal of the instrument from the valve construction and also to provide a more positive seal as pressure is applied to the outer surface of the second wall.

15. An assembly as in claim 14, wherein said inner surface extends from said plane an angle ranging from 10° to 85°.

16. An assembly as in claim 14, wherein said valve construction has a cylindrical wall between said first and second walls for forming an axially-extending bore and is provided with a reinforcing ring for reinforcing the cylindrical wall.

17. An assembly as in claim 16, wherein said reinforcing ring is disposed interior of the cylindrical wall.

18. An assembly as in claim 16, wherein said reinforcing ring is disposed within the cylindrical wall.

19. An assembly as in claim 14, together with a cylindrical cut provided in the second wall adjacent the cylindrical wall to provide hinge portions for the leaflets of the second wall.

20. An assembly as in claim 14, wherein said valve construction has a cylindrical wall between said first and second walls for forming an axially-extending bore and a liner disposed within the axially-extending bore and on the first surface of the second wall and being formed of a material which is of a higher durometer than the material of said second wall.

21. An assembly as in claim 14, together with a diaphragm, said diaphragm having a centrally disposed hub, a lock ring disposed within the hub and adapted to engage the tubular member and a threaded knob having interior threads engaging the hub for compressing the lock ring to retain the tubular member in a predetermined longitudinal position within the diaphragm and also to form a fluid-tight seal between the tubular member and the hub.

22. A valve construction for use with an introducer assembly having a tubular member with a valve housing at one end thereof for receiving the valve construction to permit a medical instrument to be introduced therethrough, the valve construction comprising a body formed of an elastic material, said body having a cylindrical wall with an axially-extending bore which has first and second ends, a first wall formed integral with the cylindrical wall and extending across the first end of the axially-extending bore, said first wall having a centrally-disposed opening therein aligned with said axially-extending bore, a second wall formed integral with the cylindrical wall and extending across the second end of the axially-extending bore, said second wall having slit therein extending diametrically of said axially-extending bore and through the second wall to provide first and second semicircular leaflets, said axially-extending bore, said opening in the first wall and said slit in the second wall when seated in said housing permitting a medical instrument to be introduced therethrough and through the tubular member with at least one seal being formed between the valve construction and the medical instrument, said second wall having inner and outer surfaces with a least the inner surface being inclined outwardly from a plane extending perpendicular to the axis of the axially-extending bore in a direction towards the axially-extending bore to avoid prolapse of the leaflets during removal of the instrument from the valve construction, means forming an arcuate hinge securing said semicircular leaflets to the cylindrical wall.

23. A valve construction for use with an introducer assembly having a tubular member with a valve housing at one end thereof for receiving the valve construction to permit a medical instrument to be introduced therethrough, the valve construction comprising a body formed of an elastic material, said body having a cylindrical wall with an axially-extending bore which has first and second ends, a first wall formed integral with the cylindrical wall and extending across the first end of the axially-extending bore, said first wall having a centrally-disposed opening therein aligned with said axially-extending bore and having a cross section which decreases in thickness in a direction towards said centrally disposed opening, a second wall formed integral with the cylindrical wall and extending across the second end of the axially-extending bore, said second wall having a single slit therein extending threrethrough diametrically of said axially-extending bore to provide first and second semicircular leaflets, said axially-extending bore, said opening in the first wall and said slit in the second wall when seated in said housing permitting a medical instrument to be introduced therethrough and through the tubular member with at least one seal being formed between the valve construction and the medical instrument, said second wall having inner and outer surfaces which are inclined outwardly from a plane extending perpendicular to the axis of the axially-extending bore in a direction towards the axially-extending bore and having a cylindrical slice therein which has an axis coincident with the axis of the axially-extending bore and extends outwardly from the inner surface to form a hinged region of reduced thickness for each of the leaflets, each of said leaflets having an arcuate base portion and a straight distal portion, said distal portion having a thickness which is less than the thickness of said base portion so as to permit the leaflets to flex and allow the instrument to pass therethrough, said distal portions of said leaflets having a substantial thickness and abutting each other to provide a keystone-like seal so as to avoid prolapse of the leaflets during removal of the instrument from the valve construction and also to provide a more positive seal as pressure is applied to the outer surface of the second wall.

* * * * *